(12) United States Patent
Boyadgis et al.

(10) Patent No.: US 12,604,942 B2
(45) Date of Patent: *Apr. 21, 2026

(54) VISUAL COMMUNICATION SYSTEM FOR A HELMET

(71) Applicant: GoPro, Inc., San Mateo, CA (US)

(72) Inventors: Alfred Boyadgis, Haymarket (AU);
Julian Chow, Haymarket (AU);
Sebastian Adams, Annandale (AU);
Joseph Azar, Five Dock (AU);
Thomas Larcher, Mosman (AU)

(73) Assignee: GoPro, Inc., San Mateo, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 18/751,807

(22) Filed: Jun. 24, 2024

(65) Prior Publication Data

US 2024/0341395 A1 Oct. 17, 2024

Related U.S. Application Data

(63) Continuation of application No. 17/602,860, filed as application No. PCT/AU2020/050386 on Apr. 20, 2020, now Pat. No. 12,016,421.

(30) Foreign Application Priority Data

Apr. 18, 2019 (AU) ................................ 2019901359

(51) Int. Cl.
*A42B 3/30* (2006.01)
*A42B 3/04* (2006.01)
(Continued)

(52) U.S. Cl.
CPC .............. *A42B 3/30* (2013.01); *A42B 3/0433* (2013.01); *A61B 5/6803* (2013.01);
(Continued)

(58) Field of Classification Search
CPC ........... A42B 3/30; A42B 3/0433; A42B 3/06; A61B 5/6803; G08B 5/36; G08G 1/0104;
(Continued)

(56) References Cited

U.S. PATENT DOCUMENTS 7,168,095 B2 1/2007 Wright
8,350,486 B2 1/2013 Bucalo
(Continued)

FOREIGN PATENT DOCUMENTS

EP 1515295 A2 3/2005
JP H09250021 9/1997
(Continued)

OTHER PUBLICATIONS

PCT International Search Report and Written Opinion, PCT Application No. PCT/AU2020/050386, Jul. 14, 2020, 12 pages.

*Primary Examiner* — John A Tweel, Jr.
(74) *Attorney, Agent, or Firm* — Young Basile Hanlon & MacFarlane, P.C.

(57) ABSTRACT

The present disclosure relates to a helmet including a shell, a housing comprising a front panel and a rear panel that form a chin portion of the shell, an electronic board disposed within the housing, a battery disposed within the housing and coupled to the electronic board, a camera disposed within the housing and coupled to the electronic board and the battery. The camera comprises a lens that extends through the front panel of the housing. The housing is embedded within an external profile shape of the helmet.

20 Claims, 6 Drawing Sheets

(51) Int. Cl.

| | |
|---|---|
| *A61B 5/00* | (2006.01) |
| *G01C 21/36* | (2006.01) |
| *G08B 5/36* | (2006.01) |
| *G08G 1/01* | (2006.01) |
| *G08G 1/09* | (2006.01) |

(52) U.S. Cl.

CPC ............. *G01C 21/365* (2013.01); *G08B 5/36* (2013.01); *G08G 1/0104* (2013.01); *G08G 1/09* (2013.01)

(58) Field of Classification Search

CPC .... G08G 1/09; G01C 21/365; G01C 21/3697; G02B 2027/0138

See application file for complete search history.

(56) References Cited

U.S. PATENT DOCUMENTS

| | | | |
|---|---|---|---|
| 9,445,639 | B1 | 9/2016 | Aloumanis |
| 9,451,802 | B2 | 9/2016 | Shearman |
| 9,737,104 | B1 | 8/2017 | Harris |
| 9,749,515 | B2 | 8/2017 | Mccauley |
| 10,368,602 | B2 | 8/2019 | Dodson |
| 11,963,572 | B2 | 4/2024 | Haristos |
| 12,016,421 | B2 | 6/2024 | Boyadgis |
| 2013/0214998 | A1 | 8/2013 | Andes |
| 2013/0257688 | A1 | 10/2013 | Yamazaki |
| 2017/0188646 | A1* | 7/2017 | Liang ..................... A42B 3/042 |
| 2017/0287441 | A1 | 10/2017 | Mckendrick |
| 2017/0329139 | A1 | 11/2017 | Shearman |
| 2021/0278666 | A1 | 9/2021 | Foley |
| 2022/0031006 | A1 | 2/2022 | Boyadgis |

FOREIGN PATENT DOCUMENTS

| | | | |
|---|---|---|---|
| JP | | 2000284214 | 10/2000 |
| JP | | 2002264874 | 9/2002 |
| JP | | 2005067367 | A | 3/2005 |
| JP | | 2009042896 | 2/2009 |
| JP | | 2015535972 | 12/2015 |
| WO | | 2012040386 | 3/2012 |

* cited by examiner

VISUAL COMMUNICATION SYSTEM FOR A HELMET

CROSS-REFERENCE TO RELATED APPLICATIONS

This application is a continuation of U.S. application Ser. No. 17/602,860, filed Oct. 11, 2021, which is a 371 of International Application PCT/AU202/050386, filed Apr. 20, 2020, which claims priority to Australian Provisional Patent Application No. 2019901359, filed Apr. 18, 2019, each of which is herein incorporated by reference in its entirety.

TECHNICAL FIELD

The present technology relates to a visual communication system for use with a helmet.

BACKGROUND

Helmets are the most important item of protection for motorcycle riders, pilots and racing car drivers. Helmet users often don't have a direct access to navigational and traffic aids as regular car drivers may have through their infotainment systems.

Helmets that provide users with aids using audio messages through speakers embedded in the helmet shell do exist in the art. However, it would be recognized that audio aids are less immediate than visual signals and may not be suitable in situations where the user needs to make a quick decision.

To address this problem, military aircraft helmets employ a head mounted display (HMD) that projects information towards the eye of the pilot to provide full situation awareness and guidance. Military helmets, however, are very expensive and HMDs are not widely used in the motorcycle or car racing industry.

The technology relates to an improved helmet.

SUMMARY

In accordance with the first aspect, the present invention provides a visual communication system for a helmet comprising: an array of light emitting devices arranged inside the helmet in a manner such that light emitted by the light emitting devices is visible to a user of the helmet; a data communication interface arranged to receive situational related data from one or more sources; and a processing module arranged to process the situational related data and control the array of light emitting devices to generate a light signal providing riding or driving guidance to the user of the helmet.

In one embodiment, the array of light emitting devices is located outside of the user field of view and the generated light signal is directed towards a peripheral vision portion of the user. The array of light emitting devices comprises a plurality of light-emitting diodes (LED) devices.

In an embodiment, the LED devices are arranged to emit light with different colors with a color being associated with one or more categories of riding/driving guidance.

In embodiments, the light emitting devices are configured to emit specific light patterns, each pattern being associated with a specific driving or riding aid.

In embodiments, the system comprises one or a combination of movement sensors, orientation sensors, positioning sensors or imaging devices. The movement sensors may comprise an accelerometer or a gyroscope; the orientation sensors may comprise an electronic compass; the positioning sensors may comprise a GPS receiver; and/or the imaging sensors may comprise one or more video-cameras. The one or more sensors may be arranged in the body of the helmet. One or more of the sensors may be external to the body of the helmet and communicate with the processing module via the data communication interface, using a wireless protocol. In some embodiments, the one or more sensors are arranged in the body of a vehicle being ridden/driven by the user.

In embodiments, the processing module is further arranged to analyze data received from the sensors in real time and provide riding/driving recommendations to the user.

In embodiments, the system comprises one or more speakers arranged to provide audio clues to the user, the audio clues being synchronized with the light signal.

In embodiments, the processing module is arranged to retrieve, via the data communication interface, traffic and/or weather-related data and process the retrieved traffic and/or weather-related data to provide improved driving or riding guidance to the user of the helmet.

In embodiments, the processing module is arranged to retrieve, via the data communication interface, rider/driver location related data and process the retrieved location related data to provide improved driving or riding guidance to the user.

In embodiments, the processing module switches between a track riding/driving mode, based on the retrieved location information, a city riding/driving mode and a mountain riding/driving mode.

In embodiments, the system further comprises a plurality of sensors located inside the helmet and arranged to measure one or more user health parameters. The one or more user health parameters may comprise one or a combination of: fatigue, focus, heart rate, pulse, eye movement, head movement.

In accordance with a second aspect, the present invention provides a helmet comprising: an impact resistant shell; a crash protection assembly including energy absorbing elements; a visual communication system in accordance with the first aspect.

In an embodiment, the array of light emitting devices and the data communication interface are arranged inside a chin portion of the helmet. The chin portion hosting the light emitting devices and the data communication interface may be waterproofed.

In embodiments, the helmet comprises a camera arranged to film the environment in the field of view of the user. A replaceable transparent shield may be used to protect the camera.

In some embodiments, the helmet comprises a crash resistant battery.

In accordance with the third aspect, the present invention comprises, a method of providing riding or driving guidance to a rider or a driver wearing a helmet that comprises a visual communication system in accordance with the first aspect; the method comprising the steps of: receiving situational related data form one or more sources via the data communication interface; processing the situational related data via the processing module; and controlling the array of light emitting devices to generate a light signal providing the rider or a driver.

In embodiments, the method further comprises the step of analyzing, via the processor, data received from the sensors in real time and provide riding/driving recommendations to the user.

Advantageous embodiments of the present invention provide an in-helmet user guidance system that provides riding/driving cues to users without the need for a heads-up display or an eye mounted display.

The riding/driving cues are provided to the user through an integrated array of light emitting devices. The emitted light is directed in the user's peripheral field of view, so the user can see the riding/driving cues while focusing in the road ahead. This allows for a fast reaction to the everchanging riding/driving environment in all riding/driving circumstances.

The system provides access to an in-helmet advanced guiding platform technology to everyday motorbike riders and racing car drivers. The array of light emitting devices and control electronics are embedded in the chin-guard of the helmet and do not alter the normal external helmet profile/shape. Being almost invisible from the outside, the system does not cause safety issues or create aerodynamic inefficiencies for the helmet. The system leverages the processing power and data communication capabilities of the user mobile communication device to minimize the amount of hardware added to the helmet and the helmet battery life.

The majority of the electronics implementing the system is located in the chin portion of the helmet. The engineering of the electronics modules in the chin portion allows for an easier and less expensive safety certification process of the helmet, as the protection requirements for the chin portion are less stringent than the shell portion.

BRIEF DESCRIPTION OF THE DRAWINGS

Notwithstanding any other forms which may fall within the scope of the present invention, to make the technology more clearly understood, an embodiment of the technology will now be described, by way of example only, with reference to the accompanying drawings in which.

DETAILED DESCRIPTION OF EMBODIMENTS

Figures 1A, 1B:
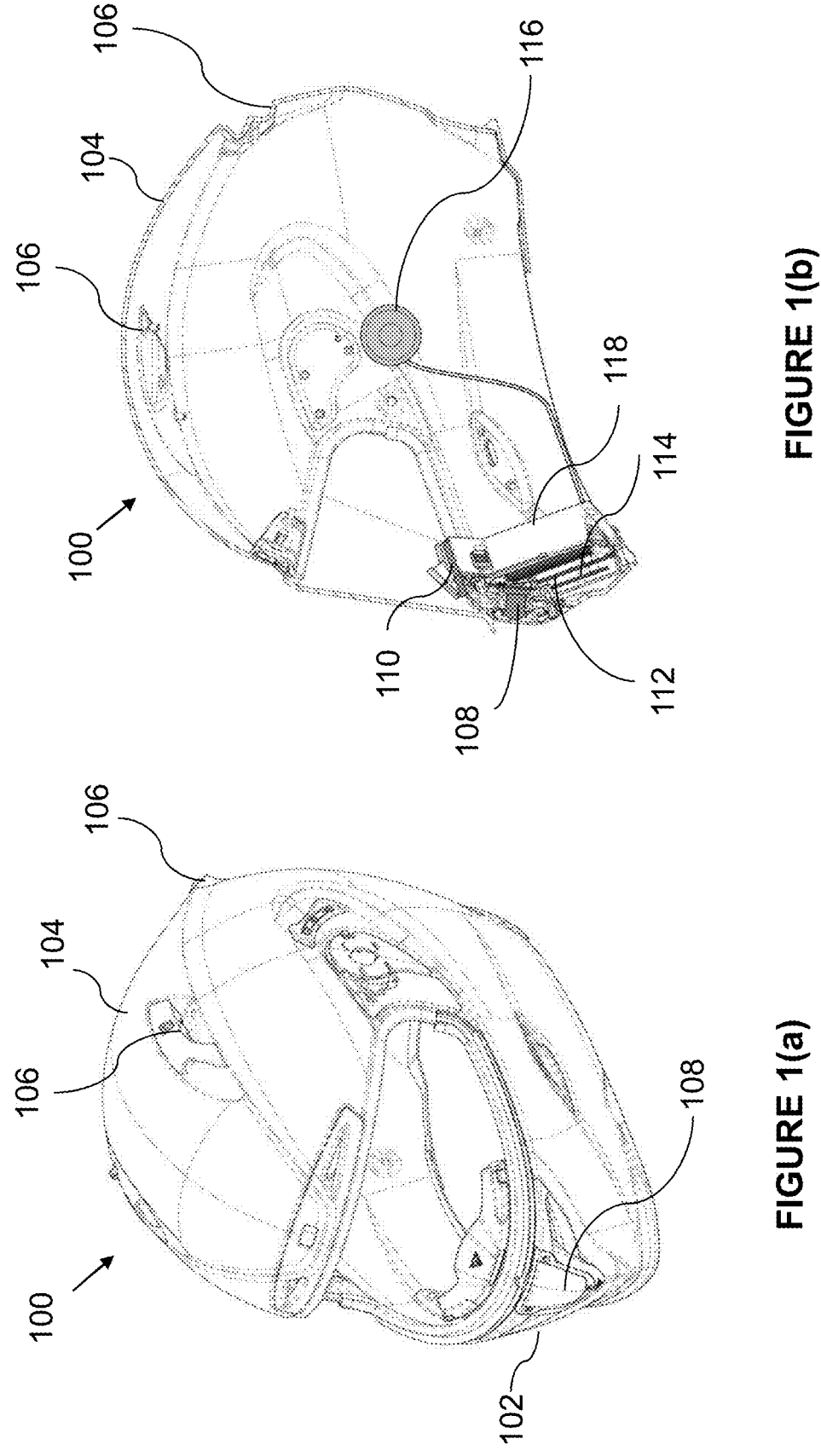
FIGS. 1(a) and 1(b) show schematic views of a motorcycle helmet embedding a system in accordance with embodiments.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

Referring now to FIG. 1 there are shown two side views of a motorcycle helmet 100 embedding a visual communication system embedded in the frontal portion of the helmet 102.

The helmet 100 has an impact absorbing shell 104, various air vents 106, and a forward mounted camera 108. The impact absorbing shell is preferably made of composite fiber. The air vents 106 allow drawing air flow into the helmet for cooling, as is especially experienced during high-speed downhill events. In embodiments, the air vents 106 may be selectively openable depending on the amount of ventilation required. The helmet 100 also comprises an internal lining for comfort purposes.

The visual communication system comprises an array of light emitting devices 110 that emit light in the visible spectrum which is visible to the helmet user. The system also comprises a camera control board 112 and a main electronic board (e.g., the main electronic board 204) that includes a data communication interface 114. The system is also connected to integrated speakers/drivers 116 that can be used to provide audio aids to the helmet user.

The riding/driving cues are provided to the users in their peripheral field of view, so the user can see the riding/driving cues while focusing in the road ahead. This allows for a fast reaction to the everchanging riding/driving environment in all riding/driving circumstances. The field of view is the outside world available to a user of a full-face helmet. If the user is directing eyes towards the road, the system is effective in their peripheral vision, therefore the users don't have to move their gaze to notice the light cues.

On full-face helmets, the viewing region is called the "eyeport". The light array is positioned so as not to obstruct the eyeport (e.g., at a lower edge of the eyeport).

The data communication interface 114 includes a Bluetooth module arranged to be paired (e.g. pairable) with a mobile communication device. In some embodiments a Wi-Fi module is also included in the communication interface 114. The data communication interface 114 is arranged to receive situational related data from one or more sources, including sensors external to the helmet 100. A processing module allows analyzing the situational related data and generating light signals providing driving or riding guidance to the user of the helmet and a memory arranged to store riding/driving and/or navigational data.

Situational data are related to the vehicle, the rider and the surrounding environment. For example, situational related data could be speed of the vehicle, lean angle, weather data, GPS data or information incoming from a network, such as the internet.

The helmet also comprises a USB-C connector that can be used to charge the system battery, located in the helmet shell, or download data from the on-board memory.

Figure 2:
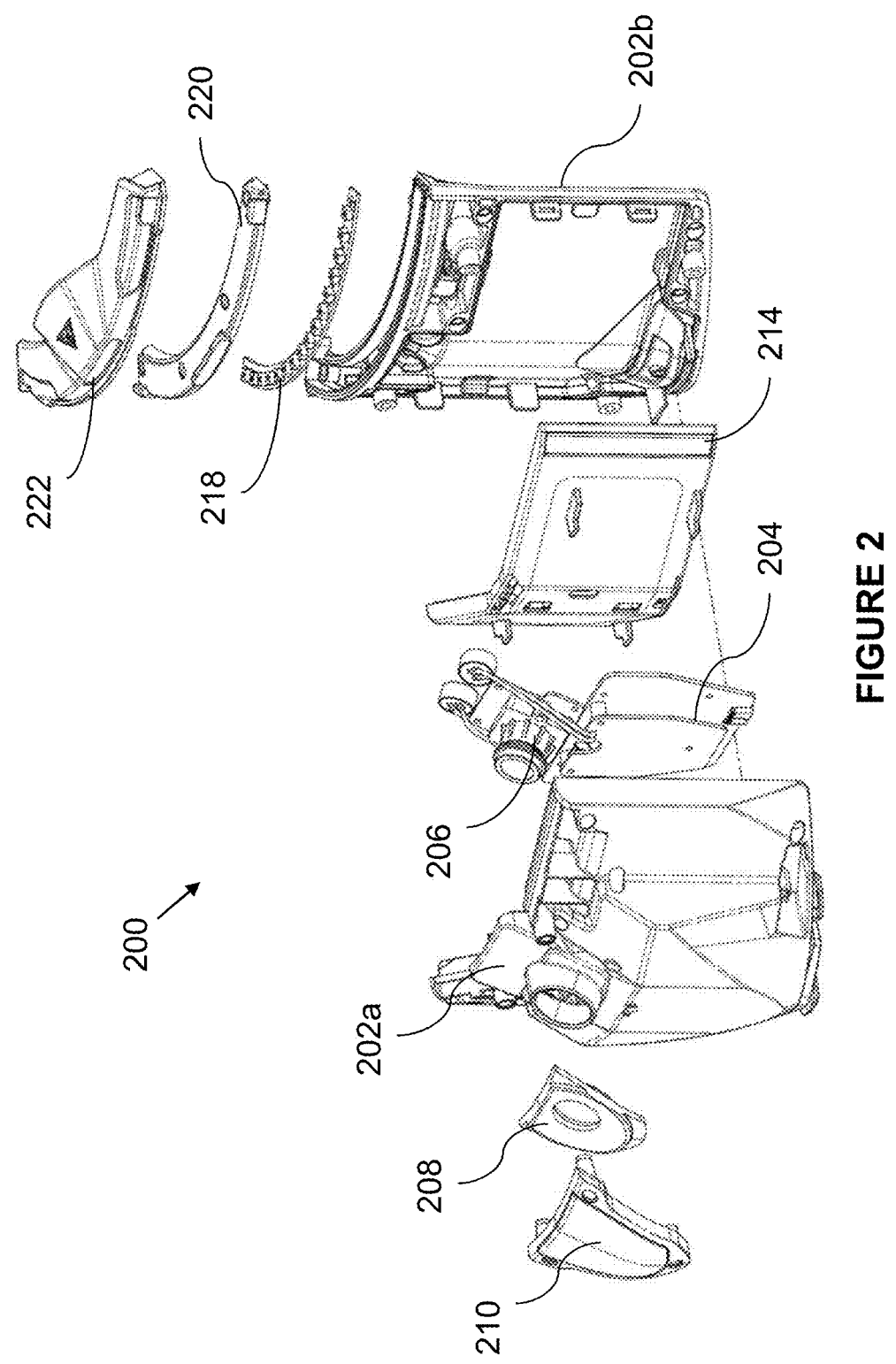
FIG. 2 shows an exploded view of a portion of the system in accordance with embodiments.

Referring now to FIG. 2, there is shown an exploded view of a visual communication module 200 in accordance with embodiments. The module 200 comprises a housing that houses the main electronic board 204 and the camera module 206 (e.g., within an interior). The housing is made of a front panel 202a and a rear panel 202b that can be releasably fastened together. A gasket 208 mounted to the front of the housing prevents water from entering in the system. The camera supports a lens protector 210 that completes the camera 206 optical path.

The module 200 also comprises a battery located in the battery housing 214 and an integrated battery control system. An array of light emitting devices, in this case a multi-color light-emitting diode (LED) array 218, lines the inner, upper edge of the helmet chin bar, delivering informational alerts via the projection of light to the rider. The array 218 supports a full spectrum of color and is paired with a waveguide 220 inside the helmet and a waveguide cover 222 in a manner such that light emitted by the light emitting devices of the array 218 is visible to the user.

The data communication interface (e.g., the data communication interface 114) is arranged on the main electronic board 204 which also comprises the processing unit and the memory, the Wi-Fi unit, the Bluetooth module, the LED array control unit, and a gyroscopic Unit.

Figure 3:
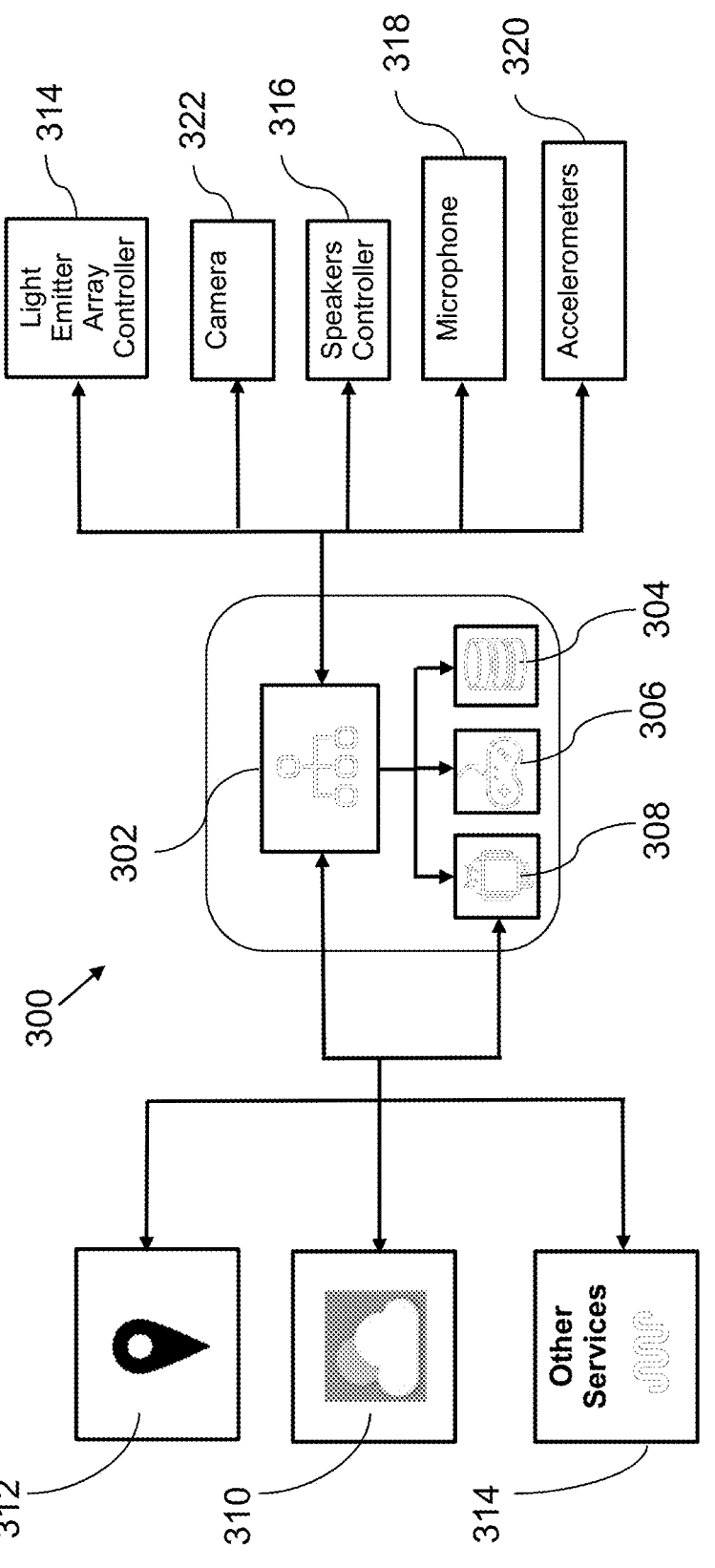
FIG. 3 shows a simplified block diagram of the visual communication system.

FIG. 3 shows a simplified block diagram 300 of a visual communication system in accordance with embodiments. The system command 302 processes information gathered via sensors and external data streams, coordinates data analysis and information sent to the helmet user via the LED array and, in some instances, the helmet speakers.

The system command 302 can be hosted entirely on a remote web server and communicate with the helmet via a mobile application 308 running on the user's mobile communication device. The system command 302 works in synergy and constant communication with a database 304, an optional controller 306 that can be located on-board the vehicle (for example handlebar of a motorbike) and the mobile application 308.

The database 304 houses all data utilized by the mobile application 308 and provides a storage location for all relevant user-generated data.

The mobile application 308 can be the single point of contact where the helmet can interact with the rich content services provided by the system command 302. The mobile application 308 is responsible for interfacing with the helmet and providing a control point for the peripherals. The mobile application 308 connects directly to the controller located on-board the vehicle 306.

The system command 302 can retrieve relevant data from a plurality of external data sources, such as weather data 310, navigational and/or traffic data 312 and/or additional data 314, such as local information and alerts. Data streams are sent to the mobile application 308 via the internet connection of the user's mobile communication device. The system command 302 is responsible for the aggregation of third-party data sources, database interaction, and computationally heavy procedures, whilst interacting directly with the mobile application 308.

Local weather forecasting data sources 310 are aggregated by the platform for the purpose of delivering location-specific weather information to the user.

Traffic and alerts data sources 312 are aggregated by the platform for the purpose of delivering location-specific traffic, hazard, and convenience information to the user.

Additional services/data sources 314 are aggregated by the platform for the purpose of delivering pertinent information to the user, relating to areas other than weather and/or traffic and alerts information.

The main electronic board (e.g., the main electronic board 204) connects to the LED array controller 314, the helmet speaker's controller 316, the microphone 318, and one or more accelerometers 320. The helmet connects directly to the mobile application 308, and is worn by the user, enabling them to leverage the on-board peripherals in conjunction with pertinent information delivered via the mobile application.

Motorbike riders have the option of controlling the peripherals and the helmet using a handlebar controller 306.

The handlebar controller 306 can interface with the helmet via mobile application 308 or directly via the helmet Bluetooth module. The handlebar controller 306 provides a selection of control functions that are central to the operation of the helmet.

The outward-facing camera 322 allows for recording and playback directly within the mobile application 308 connected to the helmet.

The LED array is controlled through controller 314 that is operated by the system command 302 through the user's mobile communication device and the software application 308. Riding/driving guidance is provided to the helmet user through the LED array and it's based on all the information gathered via the data sources (weather, traffic and others), the on-board system sensors (camera, accelerometers, gyroscope, etc.) and vehicle on-board sensors (6 axes inertial system, braking force, G-force, velocity sensors, engine temperature, oil level, gas level, brake health, suspension setting).

Figure 4:
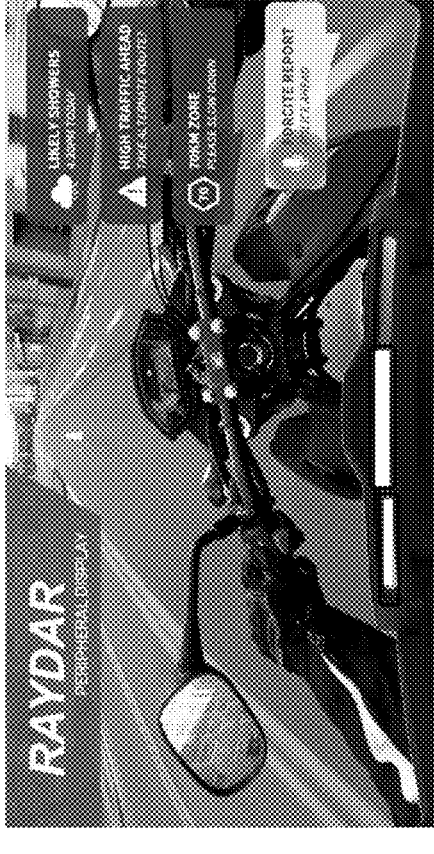
FIGS. 4(a) through 4(d) show illustrations of the in-helmet visual system in use.
Figure 4:
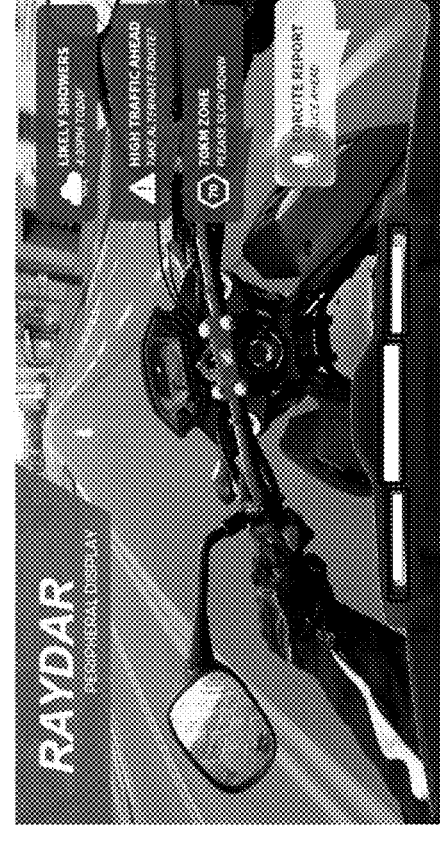
Figure 4:
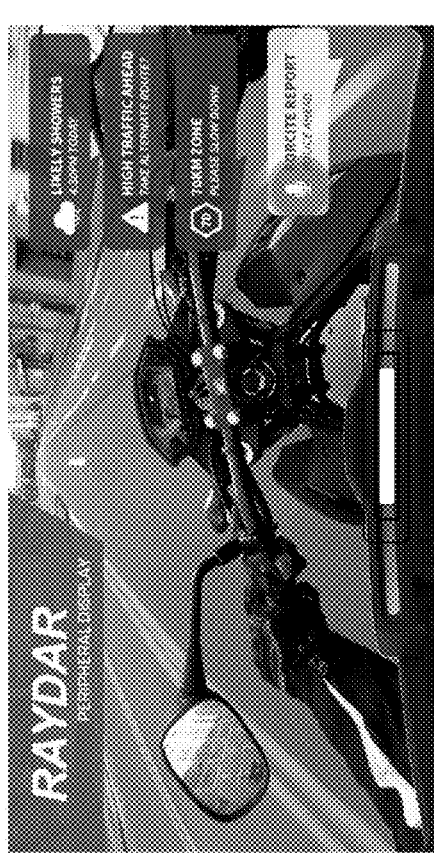
Figure 4:
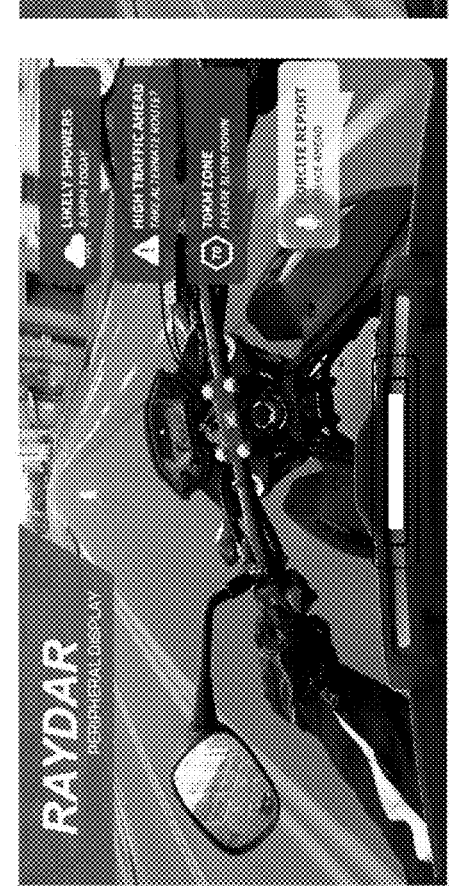

FIG. 4 shows the visual communication system of FIGS. 1 and 2 in operation. Using artificial intelligence, the system identifies the situations where it is warranted to provide riding/driving aids to the user. Lighting patterns separate each alert type, providing easily discernible meanings for each cue. The on-board speakers can also enable the mobile application to present audio cues to the rider. The audio cues are synchronized with the light patterns. The table below outlines the type of riding/driving cue provided by the helmet to the user in a number of situations.

High-importance alert: blinking red light (FIG. 4(a));

Medium-importance alert: blinking yellow light;

Navigation—turn: orange blinking (right or left side of the array (FIG. 4(b));

Police ahead: alternate blue and red (FIG. 4(c));

Weather alert: blue (FIG. 4(d)).

| | Colour | Pattern |
|---|---|---|
| Command/Audio | | |
| Helmet On | Green | Pulse once |
| Helmet Off | Red | Pulse twice |
| Battery Low | Red | Single flash |
| Helmet on charge/ charging | Green | Pulse twice once connected to power |
| Pairing mode (BT seeking) | Blue | Constant flash until paired |
| WI_FI seeking | Purple | Constant flash until paired |
| Handle bar controller connected | Blue | Blue pulse |
| Navigation | | |
| Keep left | Green | Pulse twice left side |
| Keep right | Green | Pulse twice left side |
| Turn left | Green | Transition to right 3 times |
| Turn right | Green | Transition to right 3 times |
| Exit left | Green | Pulse once left side |
| Exit right | Green | Pulse once left side |
| Continue straight | Green | Transition from outside to center twice |
| Make a U-turn | Green | From right to left twice |
| Take the 1st Exit | Green | Pulse once |
| Take the 2nd Exit | Green | Pulse twice |
| Take the 3rd Exit | Green | Pulse thrice |
| Take the 4th Exit | Green | Pulse 4 times |
| Take the 5th exit | Green | Pulse 5 times |
| Merge Left | Green | Slow Transition to the Left |
| Merge Right | Green | Slow Transition to the right |

-continued

| | Colour | Pattern |
|---|---|---|
| Alerts | | |
| Weather alert (wind, storm, flooding) | Blue | Side to side |
| Traffic ahead | Yellow | Pulse twice |
| Heavy traffic ahead | Orange | Pulse twice |
| Hazard reported on road | Red | Pulse twice |
| Speed camera reported | Purple/white | Flash twice |
| Police reported in the vicinity | Blue and Red | Pulse from red to blue |
| Sharp turns ahead proceed with caution | Orange and Yellow | Pulse from orange to yellow |
| Long straight ahead | Green | Pulse |
| Helmet | | |
| Video recording | Red | Pulse |
| Scanning area | White | Side to side |
| Mode change | | |
| Scenic mode | White | Pulse |
| Highway mode | White | Pulse |
| Street mode | White | Pulse |
| Low-light mode active | White | Pulse |
| Race mode active | Green | Pulse three times |
| Memory dump | Red | Pulse twice |

The system command stores structured information about helmet users, vehicle type, driver/rider ability and tracks user locations. Machine learning algorithms are used by the system command to provide tailored riding/guiding aids to the user through the helmet.

Different navigation type cues can be provided for different motorbike types. For example, timing of the riding aids would be different for superbike riders to delivery riders.

Sensor data collected by the helmet will determine: how frequently the user rides/drives the vehicle, braking patterns, center of balance, average speed, behavior patterns. Through machine learning, the system may learn riding/driving habits and adjust guidance accordingly. For example, for fast riders, the system may automatically turn on speed camera alerts. Storing location data allows the system to provide tailored riding/driving aids to the user by anticipating which routes the user will take and calculating travelling times.

FIG. 5 shows a number of views of the user interface provided by a software application linked to the visual communication system. The application acts as an external control system to the helmet to access complex functions and settings. Connecting the helmet to the user personal phone also allows for quick sharing to social media and also audio streaming and navigation.

Figure 5C:
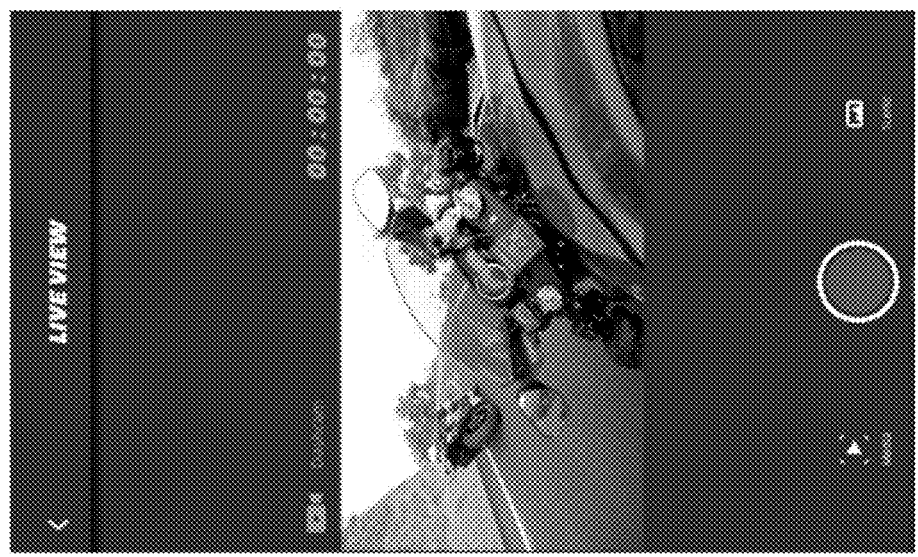
FIGS. 5(a) through 5(c) and FIGS. 6(a) and 6(b) show a number of views of the user interface provided by the software application linked to the visual communication system.
Figure 5B:
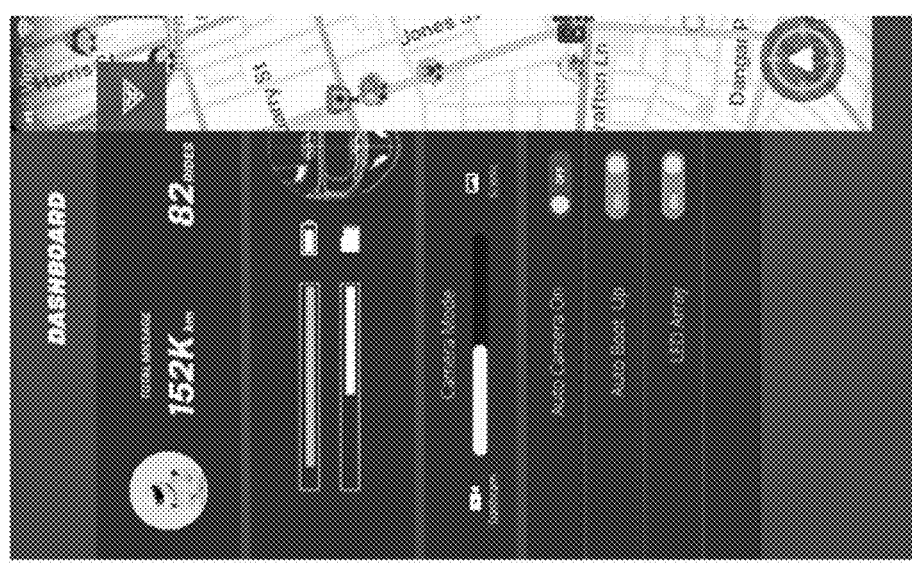
Figure 5A:
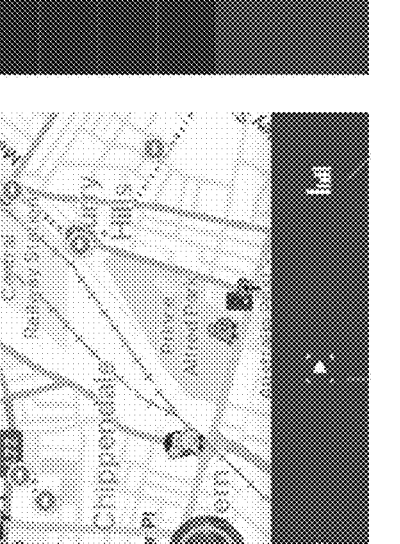

The navigation interface in FIG. 5(a) provides the rider/driver with the maps showing their current location, an address input for their destination and a shortcut to a list of favorite locations. The rider can add new locations to their location list via text input. Maps can be generated by external online and offline sources to generate map coordinates and traffic alerts, such as Mapbox, Waze, or Google.

FIG. 5(b) shows a dashboard interface that provides quick access to crucial controls and information such as helmet battery life and shortcuts to control core functions such as: camera mode, mileage counter and riding activity log that can be linked to social media profile.

FIG. 5(c) shows the live view interface or camera control page that allows the user to see preview footage from their helmet camera. The live view interface can control the status of the camera, display camera mode and time counter, and allow access to helmet media and switching between scenic mode and dashcam mode. The camera function can also activate the GPS tracking at the same time storing location data and activity data such as speed and telemetry.

Figure 6B:
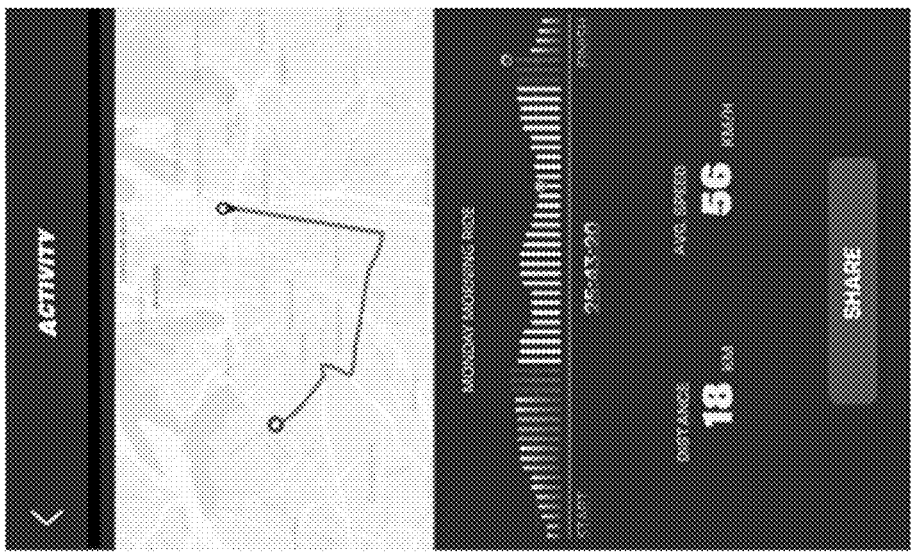
Figure 6A:
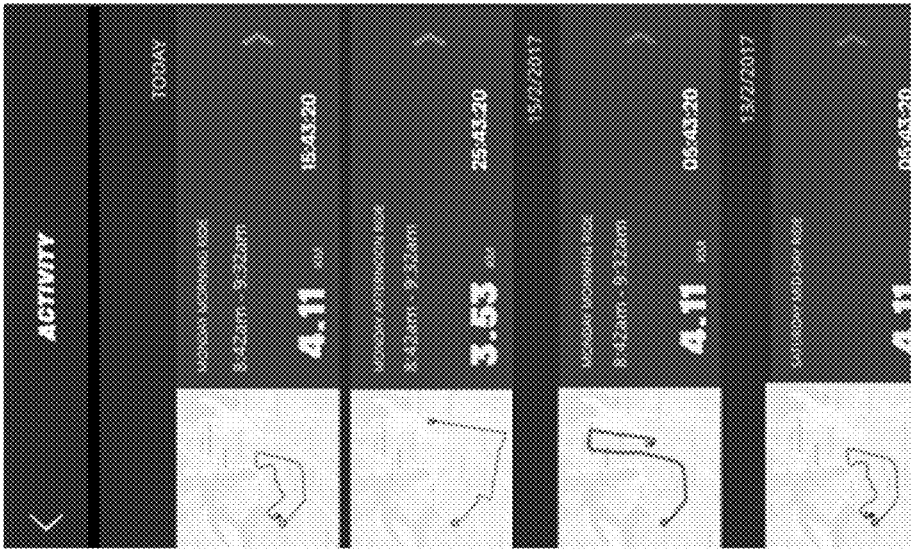

FIG. 6(a) shows the software application activity data interface. This interface shows a log of activities and routes taken while the camera has been recording from start to finish (one ride). The latest ride is displayed on the top and the user can scroll down for older rides. As each ride is correlated to a video file, the ride can be deleted by deleting the correlated video file.

FIG. 6(b) shows the software application analytics interface. By selecting one of the "rides," this interface provides a breakdown of route taken, approximate distance travelled, and a timeline of activity. A third party enabled map can zoom in and out for detailed review, and a timeline infographic shows where there is a high level of telemetry movement. For example, if high amount of lean or sudden braking is detected, it will be logged and highlighted on the timeline. Ride information can also be shared to social media.

Throughout this specification the term "comprise," or variations such as "comprises" or "comprising," will be understood to imply the inclusion of a stated element, integer or step, or group of elements, integers or steps, but not the exclusion of any other element, integer or step, or group of elements, integers or steps. The term 'consisting of' means consisting only of.

Any discussion of documents, acts, materials, devices, articles or the like which has been included in the present specification is solely for the purpose of providing a context for the present technology. It is not to be taken as an admission that any or all of these matters form part of the prior art base or were common general knowledge in the field relevant to the present technology as it existed before the priority date of each claim of this specification.

Unless the context requires otherwise or specifically stated to the contrary, integers, steps, or elements of the technology recited herein as singular integers, steps or elements clearly encompass both singular and plural forms of the recited integers, steps or elements.

In the context of the present specification the terms 'a' and 'an' are used to refer to one or more than one (i.e., at least one) of the grammatical object of the article. By way of example, reference to 'an element' means one element, or more than one element.

Those skilled in the art will appreciate that the technology described herein is susceptible to variations and modifications other than those specifically described. It is to be understood that the technology includes all such variations and modifications. For the avoidance of doubt, the technology also includes all of the steps, features, and compounds referred to or indicated in this specification, individually or collectively, and any and all combinations of any two or more of said steps, features and compounds.

It will be appreciated by persons skilled in the art that numerous variations and/or modifications may be made to the technology as shown in the specific embodiments without departing from the spirit or scope of technology as broadly described. The present embodiments are, therefore, to be considered in all respects as illustrative and not restrictive.

In a first example of an embodiment, a helmet includes a shell; a housing comprising a front panel and a rear panel that form a chin portion of the shell; an electronic board disposed within the housing; a battery disposed within the housing and coupled to the electronic board; and a camera disposed within the housing and coupled to the electronic board and the battery. The camera includes a lens that extends through the front panel of the housing, and the housing is embedded within an external profile shape of the helmet.

In the first example, the shell may define an eyeport and the chin portion of the shell may be disposed below the eyeport and configured to cover a chin of a user of the helmet. The helmet may include light sources disposed in the housing and configured to emit light toward the eyeport of the shell.

In the first example, the helmet may include a data communication interface disposed within the housing and configured to receive situational related data from one or more sources. The helmet may include a processing module configured to process the situational related data and control the light sources to generate light signals configured to provide navigational guidance to the user of the helmet.

In the first example, the helmet may include one or more speakers disposed inside the shell. The one or more speakers may be configured to provide audio cues to the user. The audio cues may be synchronized with the light signals.

In the first example, the front panel and the rear panel may be fastenable to at least one of each other or the shell to enclose the electronic board, the battery, and the camera within the housing.

In the first example, the helmet may include a gasket that surrounds the lens and is configured to prevent water from entering the housing. The helmet may include a lens protector coupled to the front panel that encloses the gasket and the lens to complete an optical path of the camera.

In a second example of an embodiment, a helmet includes a shell defining an eyeport; a housing disposed in a chin portion of the shell at a location below the eyeport; an electronic board disposed within the housing; a camera disposed within the housing and coupled to the electronic board, and comprising a lens that extends through the housing; and light sources disposed in the housing and configured to emit light toward the eyeport of the shell.

In the second example, the helmet may include a battery disposed within the housing and coupled to the electronic board, the camera, and the light sources.

In the second example, the helmet may include a processing module disposed in the housing and configured to control the light sources to generate light signals to provide navigational guidance to a user of the helmet.

In the second example, the helmet may include one or more speakers disposed inside the shell. The one or more speakers may be configured to provide audio cues to the user, the audio cues being synchronized with the light signals.

In the second example, the housing may comprise a front panel and a rear panel that are fastenable to at least one of each other or the shell to enclose the electronic board, the camera, and the light sources within the housing.

In the second example, the light sources may be configured to emit light of different colours, and wherein the different colours are associated with different categories of navigational guidance.

In the second example, the helmet may include a gasket that surrounds the lens and is configured to prevent water from entering the housing. The helmet may include a lens protector that encloses the gasket and the lens to complete an optical path of the camera.

In a third example of an embodiment, a helmet may include: a shell defining an eyeport; a housing disposed in a chin portion of the shell adjacent to the eyeport; a camera disposed within the housing; light sources disposed in the housing and configured to emit light toward a periphery of the eyeport of the shell; and a battery disposed within the housing and configured to power the camera and the light sources.

In the third example, the housing may comprise a front panel and a rear panel that are fastenable to at least one of each other or the shell to enclose the camera, the light sources, and the battery within the housing.

In the third example, the camera may comprise a lens that extends through the front panel and a lens protector configured to enclose the lens to complete an optical path of the camera, and wherein the housing is disposed within an external profile shape of the helmet.

In the third example, the helmet may include a processing module disposed in the housing and configured to control the light sources to generate light signals to provide navigational guidance to a user of the helmet.

In the third example, the helmet may include one or more speakers disposed inside the shell. The one or more speakers may be configured to provide audio cues to the user. The audio cues may be synchronized with the light signals.

In the third example, the helmet may include an electronic board disposed within the housing; and a data communication interface disposed within the housing and configured to receive situational related data from one or more sources. The processing module may be configured to process the situational related data to generate the light signals to provide the navigational guidance.

What is claimed is:

1. A helmet, comprising:
   a shell comprising an integrated chin bar that defines an eyeport;
   an electronic board disposed within an interior of the chin bar;
   a battery disposed within the interior of the chin bar and coupled to the electronic board;
   a camera disposed within the interior of the chin bar and coupled to the electronic board and the battery, the camera comprising a lens that extends through the chin bar below the eyeport; and
   light sources lining an upper edge of the chin bar at a lower edge of the eyeport, the light sources configured to emit light outside of a field of view of a user.

2. The helmet of claim 1, wherein the light sources are configured to emit the light into a peripheral field of view of the user.

3. The helmet of claim 2, wherein the light sources include a plurality of light-emitting diodes configured to emit light of different colors, and wherein the different colors are associated with different categories of navigational guidance.

4. The helmet of claim 2, further comprising:
   a data communication interface disposed within the interior of the chin bar and configured to receive situational related data from one or more sources; and
   a processing module configured to process the situational related data and control the light sources to generate light signals configured to provide navigational guidance to the user of the helmet.

5. The helmet of claim 4, further comprising:
   one or more speakers disposed inside the shell, the one or more speakers configured to provide audio cues to the user, the audio cues being synchronized with the light signals.

6. The helmet of claim 1, wherein the light sources include an array of light emitting devices paired with a waveguide.

7. The helmet of claim 1, further comprising:

a gasket that surrounds the lens and is configured to prevent water from entering the interior of the chin bar; and a lens protector coupled to the chin bar that encloses the gasket and the lens to complete an optical path of the camera.

8. A helmet, comprising:

a full-face shell defining an eyeport;

a housing disposed in a chin bar of the shell at a location below the eyeport;

an electronic board disposed within the housing;

a camera disposed within the housing and coupled to the electronic board, the camera comprising a lens that extends through the housing; and light sources disposed on an upper edge of the housing outside of a field of view of the eyeport and configured to emit light toward a periphery of the eyeport.

9. The helmet of claim 8, further comprising:

a battery disposed within the housing and coupled to the electronic board, the camera, and the light sources.

10. The helmet of claim 8, further comprising:

a processing module disposed within the housing and configured to control the light sources to generate light signals to provide navigational guidance to a user of the helmet.

11. The helmet of claim 10, further comprising:

one or more speakers disposed inside the full-face shell, the one or more speakers configured to provide audio cues to the user, the audio cues being synchronized with the light signals.

12. The helmet of claim 10, further comprising:

a data communication interface disposed within the housing and including a Bluetooth module pairable with a handlebar controller configured to control the processing module.

13. The helmet of claim 8, wherein the light sources are configured to emit light of different colors, and wherein the different colors are associated with different categories of navigational guidance.

14. The helmet of claim 8, further comprising:

a gasket that surrounds the lens and is configured to prevent water from entering the housing; and a lens protector that encloses the gasket and the lens to complete an optical path of the camera.

15. A helmet, comprising:

a shell defining an external profile of the helmet;

an eyeport defined by the shell;

a housing disposed in a chin bar of the shell adjacent to the eyeport;

a camera disposed within the housing;

an array of light emitting devices disposed on an upper portion of the housing outside of a field of view of a user;

a waveguide disposed on the upper portion of the housing and paired with the array of light emitting devices, wherein the array of light emitting devices and the waveguide are configured to project light toward a peripheral field of view of the user; and a battery disposed within the housing and configured to power the camera and the array of light emitting devices.

16. The helmet of claim 15, wherein the housing comprises a front panel and a rear panel that are fastenable to at least one of each other or the chin bar of the shell to enclose the camera, the array of light emitting devices, the waveguide, and the battery within the housing.

17. The helmet of claim 16, wherein the camera comprises a lens that extends through the front panel and the chin bar and a lens protector configured to enclose the lens to complete an optical path of the camera.

18. The helmet of claim 15, further comprising:

a processing module disposed in the housing and configured to control the array of light emitting devices to generate light signals to provide navigational guidance to a user of the helmet.

19. The helmet of claim 18, further comprising:

one or more speakers disposed inside the shell, the one or more speakers configured to provide audio cues to the user, the audio cues being synchronized with the light signals.

20. The helmet of claim 18, further comprising:

an electronic board disposed within the housing; and a data communication interface disposed within the housing and configured to receive situational related data from one or more sources, wherein the processing module is configured to process the situational related data to generate the light signals to provide the navigational guidance.

* * * * *